(12) United States Patent
Newton et al.

(10) Patent No.: US 7,014,169 B2
(45) Date of Patent: *Mar. 21, 2006

(54) ANTI-DRAWBACK MEDICAL VALVE

(75) Inventors: Brian L. Newton, Woonsocket, RI (US); Andrew L. Cote, Sr., Merrimack, NH (US); Charles F. Ganem, Cape Neddick, ME (US); Scott Castanon, Cape Neddick, ME (US)

(73) Assignee: Nypro Inc., Clinton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/844,785

(22) Filed: May 13, 2004

(65) Prior Publication Data

US 2004/0206924 A1   Oct. 21, 2004

Related U.S. Application Data

(63) Continuation of application No. 10/007,377, filed on Oct. 22, 2001, now Pat. No. 6,755,391.

(60) Provisional application No. 60/242,521, filed on Oct. 23, 2000.

(51) Int. Cl.
*F16K 51/00* (2006.01)

(52) U.S. Cl. ............... 251/149.6; 251/149.1; 604/249; 604/905

(58) Field of Classification Search ............ 251/149.6, 251/149.1; 604/249, 905
See application file for complete search history.

(56) References Cited

U.S. PATENT DOCUMENTS

| | | | |
|---|---|---|---|
| 2,594,405 A | 4/1952 | Deters | 137/53 |
| 2,693,801 A | 11/1954 | Foreman | 128/214 |
| 2,705,501 A | 4/1955 | Frizsch et al. | 137/113 |
| 2,756,740 A | 7/1956 | Deane | 128/1 |
| 2,899,975 A | 8/1959 | Fernandez | 137/543.17 |
| 2,999,499 A | 9/1961 | Willett | 128/214 |
| 3,087,492 A | 4/1963 | Garth | 128/350 |
| 3,105,511 A | 10/1963 | Murphy, Jr. | 137/399 |
| 3,192,949 A | 7/1965 | De See | 137/540 |
| 3,385,301 A | 5/1968 | Harautuneian | 128/349 |
| 3,399,677 A | 9/1968 | Gould et al. | 128/349 |
| 3,416,567 A | 12/1968 | Von Dardel et al. | 137/604 |
| 3,506,005 A | 4/1970 | Gilio et al. | 128/214 |
| 3,538,950 A | 11/1970 | Porteners | 137/608 |
| 3,570,484 A | 3/1971 | Steer | 128/214 |
| 3,572,375 A | 3/1971 | Rosenberg | 137/512 |

(Continued)

FOREIGN PATENT DOCUMENTS

EP   0268480 A1   5/1988

(Continued)

*Primary Examiner*—John Bastianelli
(74) *Attorney, Agent, or Firm*—Bromberg & Sunstein LLP

(57) ABSTRACT

A medical valve has a translating member that enlarges the volume of the interior of the valve when the valve is in an open mode (permitting fluid flow), and decreases the volume of the interior when the valve is in a closed mode (preventing fluid flow). This varying volume should substantially eliminate drawback into the valve. To that end, the valve includes a housing having an inlet and an outlet, and a fluid channel extending between the inlet and the outlet. The fluid channel includes a variable volume region. The valve further includes the above noted translating member, which is secured to the housing and at least partly bounds the variable volume region. The translating member has at least a portion that moves distally when the valve transitions from the closed mode to the open mode. The distal movement of the translating member enlarges the volume on the variable volume region.

9 Claims, 3 Drawing Sheets

U.S. PATENT DOCUMENTS

| | | | | |
|---|---|---|---|---|
| 3,726,282 A | 4/1973 | Patel | 128/349 BV |
| 3,806,086 A | 4/1974 | Cloyd | 251/149.7 |
| 3,831,629 A | 8/1974 | Mackal et al. | 137/525 |
| 3,923,065 A | 12/1975 | Nozick et al. | 128/348 |
| 3,965,910 A | 6/1976 | Fischer | 128/349 R |
| 3,994,293 A | 11/1976 | Ferro | 128/214 R |
| 4,063,555 A | 12/1977 | Ulinder | 128/214 R |
| 4,094,195 A | 6/1978 | Friswell et al. | 73/422 GC |
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149.1 |
| 4,223,808 A | 9/1980 | Williams et al. | 222/82 |
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.4 |
| 4,334,551 A | 6/1982 | Pfister | 137/614.03 |
| 4,344,435 A | 8/1982 | Aubin | 128/350 R |
| 4,401,432 A | 8/1983 | Schwartz | 604/89 |
| 4,421,296 A | 12/1983 | Stephens | 251/149.7 |
| 4,496,348 A | 1/1985 | Genese et al. | 604/167 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,661,110 A | 4/1987 | Fortier et al. | 604/256 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/329 |
| 4,683,916 A | 8/1987 | Raines | 137/854 |
| 4,698,061 A | 10/1987 | Makaryk et al. | 604/408 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Leason | 137/854 |
| 4,752,287 A | 6/1988 | Kurtz et al. | 604/99 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 604/97 |
| 4,819,684 A | 4/1989 | Zaugg et al. | 137/112 |
| 4,850,978 A | 7/1989 | Dudar et al. | 604/201 |
| 4,874,377 A | 10/1989 | Newgard et al. | 604/167 |
| 4,915,687 A | 4/1990 | Sivert | 604/83 |
| 4,917,668 A | 4/1990 | Haindl | 604/167 |
| 4,935,010 A | 6/1990 | Cox et al. | 604/122 |
| 4,966,199 A | 10/1990 | Ruschke | 137/843 |
| 5,006,114 A | 4/1991 | Rogers et al. | 604/167 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,059,175 A | 10/1991 | Hanover et al. | 604/891.1 |
| 5,080,654 A | 1/1992 | Picha et al. | 604/167 |
| 5,085,645 A | 2/1992 | Purdy et al. | 604/167 |
| 5,100,394 A | 3/1992 | Dudar et al. | 604/283 |
| 5,108,380 A | 4/1992 | Herlitze et al. | 604/283 |
| 5,147,333 A | 9/1992 | Raines | 604/249 |
| 5,171,230 A | 12/1992 | Eland et al. | 604/250 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,280,876 A | 1/1994 | Atkins | 251/149.1 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,349,984 A | 9/1994 | Weinheimer et al. | 137/543.21 |
| 5,360,413 A | 11/1994 | Leason et al. | 604/249 |
| 5,380,306 A | 1/1995 | Brinon | 604/244 |
| 5,390,898 A | 2/1995 | Smedley et al. | 251/149.6 |
| 5,401,255 A | 3/1995 | Sutherland et al. | 604/247 |
| 5,439,451 A | 8/1995 | Collinson et al. | 604/247 |
| 5,465,938 A | 11/1995 | Werge et al. | 251/149.1 |
| 5,474,536 A | 12/1995 | Bonaldo | 604/86 |
| 5,474,544 A | 12/1995 | Lynn | 604/283 |
| 5,509,433 A | 4/1996 | Paradis | 137/1 |
| 5,509,912 A | 4/1996 | Vaillancourt et al. | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,549,566 A | 8/1996 | Elias et al. | 604/167 |
| 5,569,209 A | 10/1996 | Roitman | 604/190 |
| 5,569,235 A | 10/1996 | Ross et al. | 604/403 |
| 5,573,516 A | 11/1996 | Tyner | 604/249 |
| 5,578,059 A | 11/1996 | Patzer | 604/249 |
| 5,616,129 A | 4/1997 | Mayer | 604/167 |
| 5,616,130 A | 4/1997 | Mayer | 604/167 |
| 5,620,434 A | 4/1997 | Brony | 604/406 |
| 5,674,206 A | 10/1997 | Allton et al. | 604/249 |
| 5,676,346 A | 10/1997 | Leinsing | 251/149.1 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A | 12/1997 | Lopez | 604/249 |
| 5,749,861 A | 5/1998 | Guala et al. | 604/249 |
| RE35,841 E | 7/1998 | Frank et al. | 604/256 |
| 5,806,831 A | 9/1998 | Paradis | 251/149.1 |
| 5,820,601 A | 10/1998 | Mayer | 604/167 |
| 5,921,264 A | 7/1999 | Paradis | 137/15 |
| 6,029,946 A | 2/2000 | Doyle | 251/149.1 |
| 6,036,171 A | 3/2000 | Weinheimer et al. | 251/149.1 |
| 6,039,302 A | 3/2000 | Cote, Sr. et al. | 251/149.1 |
| 6,048,335 A | 4/2000 | Mayer | 604/167 |
| 6,050,978 A | 4/2000 | Orr et al. | 604/249 |
| 6,068,011 A | 5/2000 | Paradis | 137/1 |
| 6,089,541 A | 7/2000 | Weinheimer et al. | 251/149.6 |
| 6,152,900 A | 11/2000 | Mayer | 604/167 |
| 6,245,048 B1 | 6/2001 | Fangrow, Jr. et al. | 604/249 |
| 6,290,206 B1 | 9/2001 | Doyle | 251/149.1 |
| 6,344,033 B1 | 2/2002 | Jepson et al. | 604/256 |
| 6,428,520 B1 | 8/2002 | Lopez et al. | 604/249 |
| 6,543,745 B1 | 4/2003 | Enerson | 251/149.7 |
| 6,595,964 B1 | 7/2003 | Finley et al. | 604/249 |
| 6,609,696 B1 | 8/2003 | Enerson | 251/86 |
| 2003/0098430 A1 | 5/2003 | Leinsing et al. | 251/149.6 |
| 2003/0141477 A1 | 7/2003 | Miller | 251/149.1 |

FOREIGN PATENT DOCUMENTS

| | | |
|---|---|---|
| EP | 0629418 A1 | 12/1994 |
| GB | 2 079 162 | 1/1982 |
| GB | 01/20218 A1 | 3/2001 |
| WO | 83/02559 | 8/1983 |
| WO | 93/11828 | 6/1993 |
| WO | 96/00107 | 1/1996 |
| WO | 97/39791 | 10/1997 |
| WO | 98/22178 | 5/1998 |
| WO | 98/26835 | 6/1998 |
| WO | 98/39594 | 9/1998 |
| WO | 00/44433 | 8/2000 |

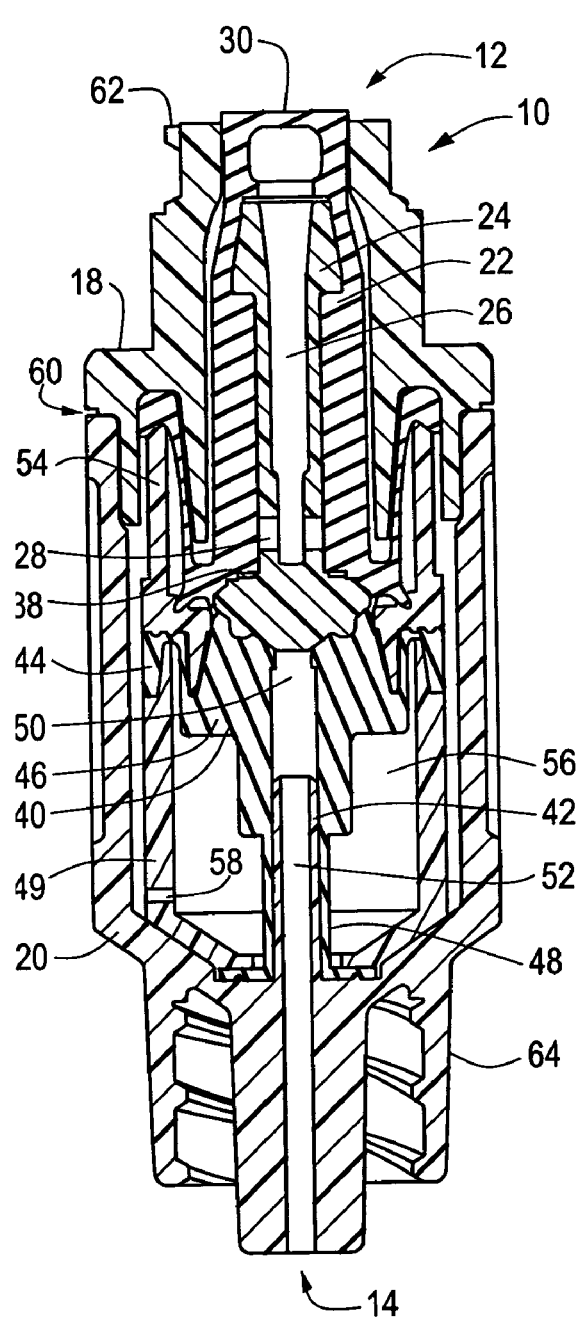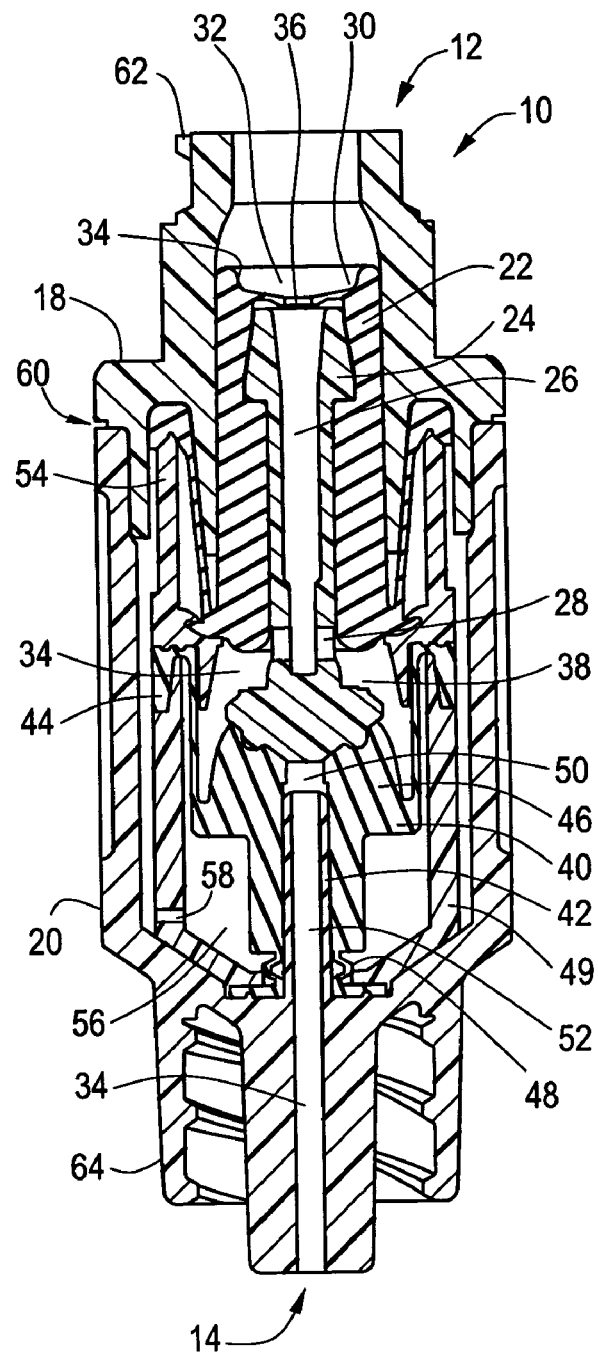
*FIG. 2A*  *FIG. 2B*

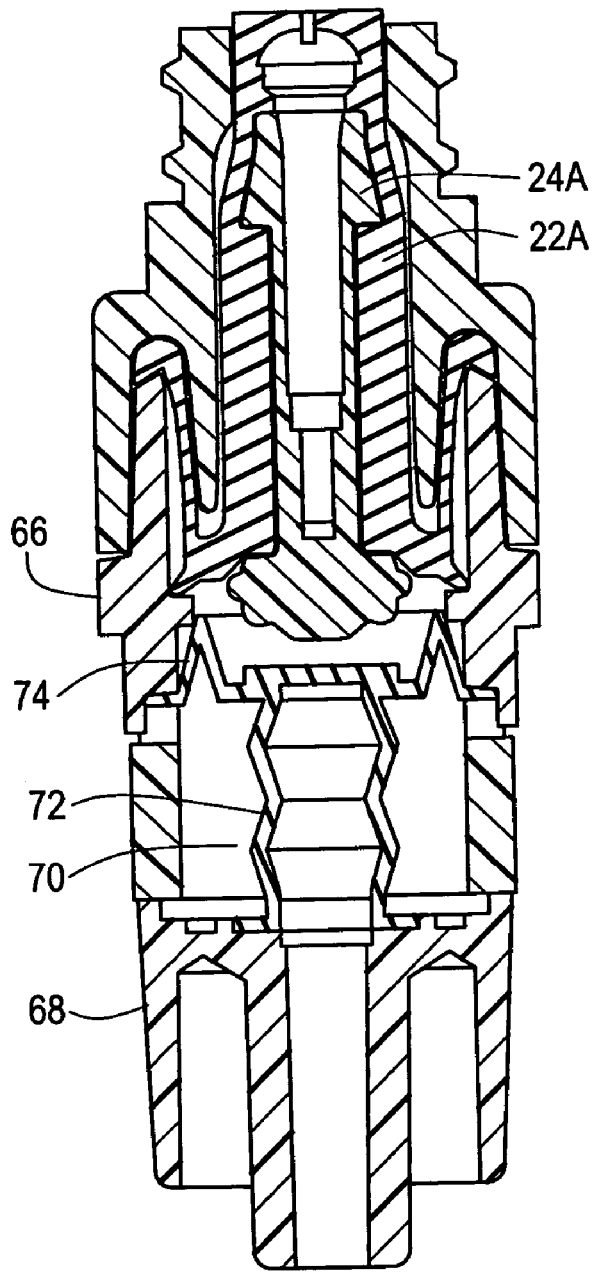 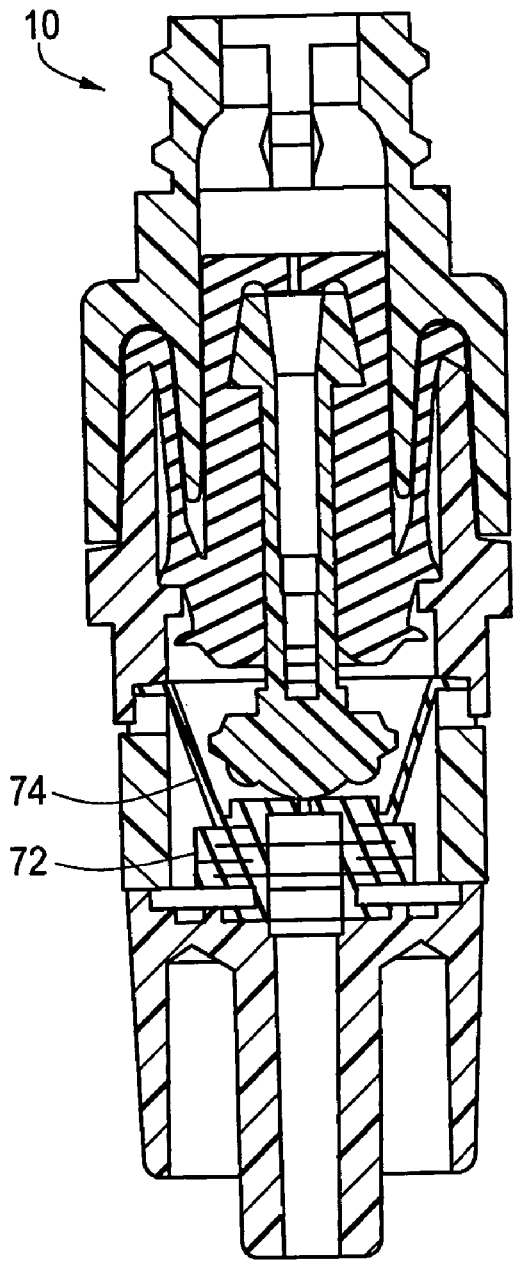
*FIG. 3A*      *FIG. 3B*

ANTI-DRAWBACK MEDICAL VALVE

PRIORITY

This patent application is a continuation patent application of U.S. patent application Ser. No. 10/007,377 now U.S. Pat. No. 6,755,391, filed Oct. 22, 2001, the disclosure of which is incorporated herein, in its entirety, by reference.

Co-pending U.S. patent application Ser. No. 10/007,377 claims priority from U.S. provisional patent application No. 60/242,521, filed Oct. 23, 2000, the disclosure of which is incorporated herein, in its entirety, by reference.

This patent application claims priority from both U.S. provisional patent application No. 60/242,521 and U.S. patent application Ser. No. 10/007,377.

FIELD OF THE INVENTION

The invention generally relates to medical products and, more particularly, the invention relates to devices for reducing backflow through a medical valve.

BACKGROUND OF THE INVENTION

Medical valving devices commonly are utilized to valve fluids injected into and withdrawn from a patient. One exemplary type of medical valving device, known in the art as a "catheter introducer," maintains a sealed-port for accessing the patient's vasculature. Use of such a valve enables vascular access without requiring the patient's skin to be repeatedly pierced by a needle. Moreover, catheter introducers are constructed to withstand a range of backpressures produced by a patient's blood pressure, thus minimizing blood loss resulting from fluid injections or withdrawals.

Fluid commonly is transferred to/from a patient by inserting a syringe into a medical valve, thus communicating with the patient's vasculature. Problems arise, however, when the syringe is withdrawn from the valve. More particularly, a back pressure produced by withdrawing the syringe undesirably can cause blood to leak proximally into various parts of the valve. In addition to coagulating and impeding the mechanical operation of the valve, blood in the valve also compromises the sterility of the valve.

SUMMARY OF THE INVENTION

In accordance with one aspect of the invention, a medical valve has a translating member that enlarges the volume of the interior of the valve when the valve is in an open mode (permitting fluid flow), and decreases the volume of the interior when the valve is in a closed mode (preventing fluid flow). This varying volume should substantially eliminate drawback into the valve. To that end, the valve includes a housing having an inlet and an outlet, and a fluid channel extending between the inlet and the outlet. The fluid channel includes a variable volume region. The valve further includes the above noted translating member, which is secured to the housing and at least partly bounds the variable volume region. The translating member has at least a portion that moves distally when the valve transitions from the closed mode to the open mode. The distal movement of the translating member enlarges the volume on the variable volume region.

In some embodiments, the translating member is substantially coaxial with the majority of the fluid channel. The translating member may include a securing portion that normally maintains the noted portion of the translating member in a position that minimizes the volume of the variable volume region. In such case, the securing portion may stretch when the valve transitions from the closed mode to the open mode, and retract when the valve transitions from the open mode to the closed mode.

The valve also may include a guide member extending into the translating member. The guide member may include at least a portion of the fluid channel. The fluid channel may include a translating fluid channel extending through the translating member. The translating fluid channel illustratively has substantially the same shape in both the open and closed modes.

In some embodiments, the translating member comprises a bellows. In other embodiments, the translating member may include a compressible portion that compresses when the valve transitions from the closed mode to the open mode. Among other things, the valve may include a swabbable seal, and/or may be a luer activated valve.

In a manner similar to the above noted aspect of the invention, other aspects of the invention include a medical valve (having an open mode that permits fluid flow and a closed mode that prevents fluid flow) that also has a translating member. The valve is capable of transitioning between the open mode and the closed mode, and includes a housing having an interior with a primary fluid channel with a variable volume region. The noted translating member bounds the variable volume region and is secured to the interior of the housing. The translating member has a translating member fluid channel that permits fluid flow through the translating member. The primary fluid channel thus includes the translating member fluid channel. At least a portion of the translating member longitudinally moves when the valve transitions from the closed mode to the open mode. Such longitudinal movement enlarges the volume of the variable volume region.

BRIEF DESCRIPTION OF THE DRAWINGS

The foregoing and advantages of the invention will be appreciated more fully from the following further description thereof with reference to the accompanying drawings wherein:

FIG. 2A schematically shows a first embodiment of the medical valve shown in FIG. 1 along line X—X in a closed mode.

FIG. 2B schematically shows the first embodiment of the medical valve shown in FIG. 1, but in an open mode.

FIGS. 3A and 3B schematically show a second embodiment of the medical valve shown in FIG. 1 along line X—X, where FIG. 3A shows this embodiment in a closed mode, while FIG. 3B shows this embodiment in an open mode.

DESCRIPTION OF ILLUSTRATIVE EMBODIMENTS

Figure 1:
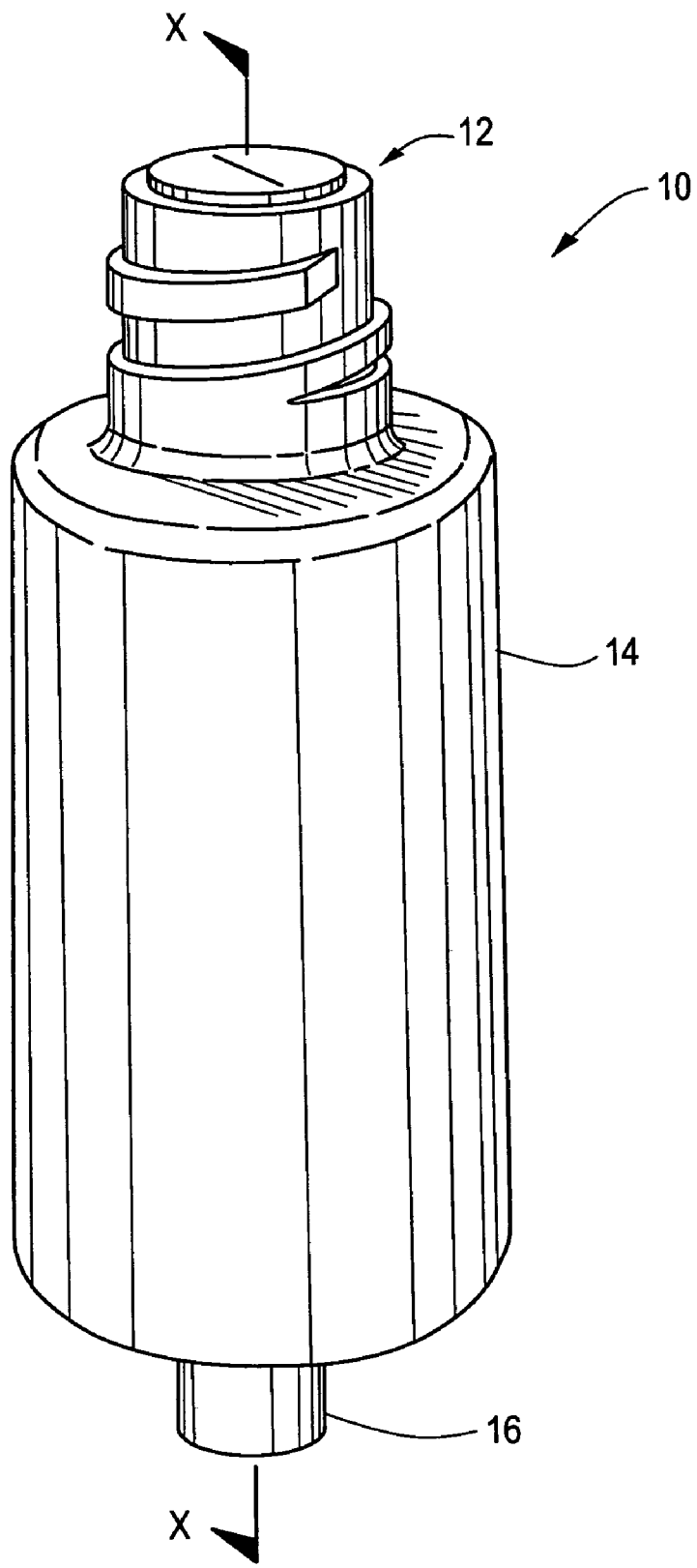
FIG. 1 schematically shows a medical valve configured in accordance with illustrative embodiments of the invention.

In illustrative embodiments of the invention, a medical valve is configured to substantially eliminate fluid drawback when a nozzle or syringe is withdrawn from it. In fact, various embodiments of the invention provide a distally directed positive pressure when moving from an open position (i.e., an open mode permitting fluid flow) to a closed position (i.e., a closed mode preventing fluid flow), thus substantially preventing any fluid drawback. To these ends, illustrative embodiments generally include a medical valve with an interior fluid chamber that is larger when the valve is in an open position than when the valve is in a closed position. Details of various embodiments are discussed below.

FIG. 1 schematically shows a medical valve 10 that is configured to reduce fluid drawback (a/k/a "back-flow") when a syringe or other type of nozzle is withdrawn from it. The valve 10 includes a proximal port 12 for receiving the nozzle, a valve body 14 having an internal valve mechanism (shown in FIGS. 2A, 2B, 3A, and 3B) that controls fluid flow through the valve 10, and a distal port 16 for directing fluid between the valve 10 and a patient. The fluid preferably is in liquid form, such as liquid medication. Although much of the discussion herein refers to the proximal port 12 as a fluid inlet, and the distal port 16 as a fluid outlet, the proximal and distal ports 12 and 16 also may be respectively utilized as outlet and inlet ports.

In illustrative embodiments, the valve 10 is similar to the luer-activated swab valve disclosed in U.S. Pat. No. 6,039,302 entitled, "SWABBABLE LUER-ACTIVATED VALVE," the disclosure of which is incorporated herein, in its entirety, by reference. Of course, various embodiments may relate to other types of valves and thus, such embodiments are not limited to swab valves and/or luer-activated valves. Other embodiments are related to those shown in pending U.S. patent application Ser. Nos. 09/479,327 and 09/812,237, the disclosures of which also are incorporated herein, in their entireties, by reference.

FIG. 2A schematically shows one embodiment of the medical valve 10 (shown in FIG. 1 along line X—X) in a closed position. As noted above, this embodiment illustratively provides a positive, distally-directed pressure as the valve 10 transitions from the open position to the closed position.

In summary, the valve 10 includes an inlet housing portion 18 (having the proximal port 12) that is coupled with an outlet housing portion 20 (having the distal port 16). When coupled, the two housing portions 18 and 20 produce the above noted valve body 14. A valve mechanism located within the interior of the housing provides the primary function of the valve 10; namely, selectively permitting fluid flow through the valve 10. In illustrative embodiments, the valve mechanism is a luer-activated valve. In other words, the valve mechanism is opened upon application of a distally directed force by a nozzle, syringe, or other fluid carrying instrument conventionally used for such purposes. Also in illustrative embodiments, the valve mechanism is swabbable (i.e., the valve mechanism has a surface flush with the proximal port 12 for facilitating cleaning with a swab or other apparatus). It should be reiterated, however, that embodiments of the invention can be applied to other types of valves.

To effectively perform its basic valving function, the valve mechanism includes a stretchable and compressible gland 22 secured within the housing interior, and a rigid, longitudinally movable cannula 24 secured within the valve 10 by the gland 22. The gland 22 and cannula 24 cooperate to selectively permit fluid flow through the valve 10. To that end, the cannula 24 forms a cannula channel 26 that terminates at a transverse channel 28. The transverse channel 28 in turn normally is occluded by the gland 22. Consequently, when transitioning from the closed position to the open position, the cannula 24 moves relative to the gland 22 until the transverse channel 28 is not occluded by the gland 22. In other words, the cannula 24 and gland 22 move in a manner similar to the segments of a telescope. As shown in FIG. 2B, this relative movement permits fluid flow through the valve 10.

The gland 22 also includes a proximally located pierced seal section 30 (having an aperture 32) that normally is flush with the proximal port 12 (noted above). When a nozzle applies a distally directed force to the outer face of the seal section 30, the aperture 32 opens, consequently permitting fluid communication with the cannula channel 26. In illustrative embodiments, this seal section 30 acts as a low pressure seal, while the transverse channel 28/gland 22 interface act as a high pressure seal. The high pressure seal thus can withstand larger back pressures than the low pressure seal.

The interior of the valve 10 effectively forms a main channel 34 that, when in the open position, extends between the proximal port 12 and the distal port 16. As shown in FIGS. 2A and 2B, the main channel 34 includes a plurality of segments. Those segments include the area bounded by the proximal end of the cannula 24 and the seal section 30 (referred to herein as the "seal channel 36"), the cannula channel 26 (including the transverse channel 28), and several other segments. Each of these segments is discussed below.

In accordance with illustrative embodiments, one of these several other channel segments is a variable volume region 38 that expands when the valve 10 transitions from the closed position to the open position. In a corresponding manner, the variable volume region 38 contracts when the valve 10 transitions from the open position to the closed position. Stated another way, the volume of the variable volume region 38 is greater when the valve 10 is in the open position than when the valve 10 is in the closed position. To these ends, the valve mechanism also includes a flexible and compressible translating member 40 that provides a movable boundary for the variable volume region 38, and a fixed guide member 42 for supporting and guiding the translating member 40.

The translating member 40 includes a plurality of different sections. In particular, the translating member 40 includes a securing portion 44 that functions as a spring for the entire translating member 40 (continually providing a proximally directed force), a movable portion 46 for moving longitudinally within the housing interior to vary the size of the variable volume region 38, and a compressible portion 48 that circumscribes the guide member 42.

The compressible portion 48 compresses (i.e., moves) when the movable portion 46 moves. The inner diameter of the compressible portion 48 thus is sized to be sufficiently larger than the outer diameter of the guide member 42 to ensure that a negligible frictional resistance is produced when the compressible portion 48 is compressed and/or expanded. In addition, the portion of the movable portion 46 circumscribing the guide member 42 also is sized in a corresponding manner. This sizing produces a space between the guide member 42 and the movable/compressible portions 46 and 48 into which fluid can leak. Fluid that leaks into this space nevertheless is sealed by a first liner 49 (discussed in greater detail below).

As shown in FIGS. 2A and 2B, the translating member 40 also includes a translating channel 50 extending through the movable portion 46, while the guide member 42 includes a guide channel 52 that leads to the distal port 16. Consequently, in addition to the segments discussed above, the main channel 34 also includes the translating channel 50 and the guide channel 52. Accordingly, in summary, the main channel 34 includes the seal channel 36, the cannula channel 26 (including the transverse channel 28), the variable volume region 38, the translating channel 50, and the guide channel 52.

While the volume and shape of some other segments of the main channel 34 may vary to some extent, the varying volume of the variable volume region 38 is the primary means for providing the function of reducing and/or effectively eliminating drawback in the valve 10. It should be noted that in illustrative embodiments, the translating channel 50 maintains a substantially constant shape as the valve 10 transitions between the open and closed modes. Of course, some negligible deformation may take place to such channel 50, but such deformation should not affect the anti-drawback performance of the valve 10.

The translating member 40 is secured within the housing interior by two mechanical press-fit connections. In particular, the compressible portion 48 is secured to the bottom wall of the housing interior by a distal end of the above noted first liner 49, while the securing portion 44 is secured between the proximal end of the first liner 49 and the distal end of a second liner 52. As noted above, the connection of the compressible portion 48 with the first liner 49 preferably acts as a seal to prevent fluid from leaking from the space between the compressible portion 48 and the guide member 42.

In like manner, the gland 22 is partially secured within the housing interior by a mechanical press fit between the proximal end of the second liner 52 and an inner surface of the inlet housing portion 18. Both the immediately noted press fits of the gland 22 and securing portion 44 seal the variable volume region 38. Consequently, among other things, the variable volume region 38 is sealingly bounded by the gland 22, securing portion 44, their noted press-fit connections, and the second liner 52. Fluid received in the variable volume region 38 from the cannula channel 26 thus is directed into the translating channel 50. Note that the bulbous distal end of the cannula 24 illustratively has grooves (not shown) to permit fluid flow into the translating channel 50. Its direct contact with the translating member 40 thus should not occlude fluid flow.

To operate effectively, the translating member 40 should have some space into which it can move. Specifically, when transitioning from the closed position to the open position, the movable portion 46 requires some space into which it can move. To that end, an annular region between the first liner 49 and the translating member 40 (shown in FIGS. 2A and 2B as reference number 56) permits the compressible portion 48 and the movable portion 46 such freedom of movement.

Unless the annular region 56 is vented, however, such movement may encounter a relatively significant mechanical resistance. To overcome this resistance, the first liner 49 includes a vent 58 that leads to the exterior of the valve 10 via a space between the it and the housing interior, and the connection point of the two housing portions 18 and 20 (i.e., this point is known in the art as a "reveal," and identified by reference number 60).

In alternative embodiments, no annular region is used. Instead, the movable portion 46 is compressible, thus enlarging the variable volume region 38 when in the open position as it is compressed.

FIG. 2A shows the translating member 40 in its normal position (i.e., in the closed position). As noted above, when in this position, the valve 10 is closed. FIG. 2B, however, shows the translating member 40 in the open position. Specifically, as a nozzle is inserted through the proximal port 12, the seal section 30 deforms to open the aperture 32, and the cannula 24 is urged distally. The bulbous distal end of the cannula 24 correspondingly begins applying a distally directed force to the movable portion 46 of the translating member 40. When a sufficient force is applied to overcome the proximal bias provided by the securing portion 44, the movable portion 46 begins longitudinally moving in a distal direction over the guide member 42. In addition to stretching the securing portion 44, this force compresses the compressible portion 48. In some embodiments, the compressible portion 48 bows outwardly into the annular region. In other embodiments, the compressible member compresses in a manner similar to a bellows.

As the movable portion 46 moves distally, the variable volume region 38 enlarges, thus filling with fluid from the nozzle. In the embodiment shown in FIGS. 2A and 2B, the valve 10 has no positive stop to limit movement of the cannula 24. Nevertheless, the valve 10 is sized and configured so that the transverse channel 28 is out of occluding contact with the gland 22 well before it can contact the proximal portion of the guide member 42. For example, in some embodiments, to move the transverse channel 28 from occluding contact with the gland 22, the distal end of the cannula 24 longitudinally moves less than half the distance toward the guide member 42 from its closed position.

As the nozzle is withdrawn from the proximal port 12, the distally directed force decreases, thus causing the movable portion 46 to be urged back toward its closed position shown in FIG. 2A. Specifically, the securing portion 44 acts as a spring by providing a constant proximally directed force to the movable portion 46. Consequently, as the movable portion 46 retracts proximally, the volume of the variable volume region 38 decreases to reduce the overall volume of the entire main channel 34. This reducing volume causes a positive pressure to be exerted through the distal port 16. This positive pressure forces fluid from the variable volume region 38 (i.e., and from other segments of the main channel 34), consequently ensuring that no fluid is drawn back into the valve 10.

The valve 10 may be manufactured from commercially available materials conventionally used for these purposes. For example, the housing portions 18 and 20, guide member 42, cannula 24, and the first and second liners 49 and 52 may be manufactured from a rigid, medical grade thermoplastic. In illustrative embodiments, the guide member 42 is integral with the outlet housing portion 20. Accordingly, the outlet housing portion 20 illustratively is molded to include the integral guide member 42. During manufacture of the valve 10, the two housing portions may be coupled by means of conventional ultrasonic welding processes. In other embodiments, the two housing portions may be snap-fit together.

As noted above, the gland 22 and translating member 40 illustratively are manufactured from a flexible and compressible medical grade elastomeric material. By way of example, these elements may be manufactured from silicon and rubber, among other materials.

Alternative embodiments of the valve 10 shown in FIGS. 2A and 2B omit some of the discussed elements. For example, the guide member 42 may be omitted if the translating member 40 is manufactured from a material and configured in a manner that does not require annular support. Additionally, the gland 22 and translating member 40 may be combined into a single, large flexible and compressible member. In such case, the first and second liners 49 and 52 can be omitted. In such embodiment, the various connections within the housing interior for the larger flexible and compressible member may be modified to accommodate the different geometry.

In still other embodiments, the distal end of the cannula 24 can be a different shape. For example, the distal end of the cannula 24 can be flat, but have ridges or grooves to permit fluid flow to the translating channel 50. In other embodiments, the distal end of the cannula 24 can be normally retracted so that it does not normally contact the translating member 40. In such case, when transitioning to the open position, the cannula 24 longitudinally moves distally some distance before the volume of the variable volume region 38 begins to increase.

FIGS. 2A and 2B show additional features of the disclosed valve 10. Such additional features include threads 62 to lock a nozzle or luer, and a distally located threaded skirt 64 to lock onto another valve or similar device FIGS. 3A–3B schematically show a second embodiment of the valve 10 shown in FIG. 1. This embodiment has many elements that are similar to those shown in the first embodiment. For example, this embodiment has inlet and outlet housing portions 18A and 20A, a gland 22A with an apertured seal section 30A, and a cannula 24A. In fact, this embodiment also includes a main channel 34A with a variable volume region 38A. Accordingly, many such elements are not discussed in detail below.

Unlike the first embodiment shown in FIGS. 2A and 2B, the outlet housing portion 20A of this embodiment includes a first portion 66 and a second portion 68. The first portion 66 secures directly to the inlet housing portion 18 to secure the gland 22A within the valve 10, while the second portion 68 secures to the distal end of the first portion 66 to lock a mechanically collapsible element ("collapsible element 70") within the valve 10.

The collapsible element 70 collapses as the cannula 24A is urged distally. When the collapsible element 70 is collapsed, the variable volume region 38A has a volume that is greater than when the collapsible element 70 is not collapsed. Among other things, the collapsible element 70 includes a bellows 72. The collapsible element 70 also includes a securing ring 74 that acts as a spring. Specifically, the securing ring 74 normally applies a proximally directed force to the remainder of the collapsible element, thus normally biasing such element in a non-collapsed state. In illustrative embodiments, the securing ring 74 is locked between the first and second portions 46 and 48 of the outlet housing.

The distal end of the cannula 24A normally is not in contact with the proximal end of the collapsible element 70. Instead, the distal end of the cannula 24A normally is retracted somewhat from the proximal end of the collapsible element 70. When the valve 10 begins to open, the cannula 24A contacts the proximal end of the collapsible element 70 to mechanically compress the bellows 72 (see FIG. 3B). The collapsible element 70 preferably is manufactured from a stretchable, flexible material so that it is forced proximally by the securing ring 74 as the cannula 24A retracts proximally.

When fully open, the transverse channel 28 is not occluded by the gland 22A. In addition, the proximal end of the collapsible element 70 includes a plurality of slits (not shown) that permit fluid to flow around the cannula 24A, and into its interior (via a bellows channel 50A). Fluid exits the valve 10 via the output port.

Various dimensions for the elements of this second embodiment may be as follows:
Maximum outer diameter of inlet housing: 0.46 inches;
Length of second portion of outlet housing: 0.68 inches;
Total length of valve 10: 1.37 inches; and
Width of distal port 14: 0.08 inches.

Although these dimensions are discussed as potential dimensions, they are not intended to limit the scope of the invention. Nevertheless, these dimensions are useful in estimating fluid volume within the variable volume region 38A. It has been determined, on paper, that when closed (FIG. 3A), a valve 10 with these dimensions should have an interior volume (for containing fluid) of about 0.144 cubic centimeters. This interior volume includes the variable volume region 38A and the outlet path located distally of the collapsible member 56. When open (FIG. 3B), it has been determined, on paper, that a valve 10 with these dimensions should have an interior volume (for containing fluid) of about 0.18 cubic centimeters. Accordingly, since the interior fluid volume is greater when open than when closed, the valve 10 should expel fluid as it retracts toward the closed position.

This embodiment illustratively may be snap-fit together, or coupled by other known means. For example, the valve 10 may be ultrasonically welded in accordance with conventional welding techniques. When coupled, the gland 22A is secured between the inlet and outlet housing 18 and 20 by notches 66 that extend directly into the gland 22A.

Although various exemplary embodiments of the invention are disclosed below, it should be apparent to those skilled in the art that various changes and modifications can be made that will achieve some of the advantages of the invention without departing from the true scope of the invention. These and other obvious modifications are intended to be covered by the claims that follow.

We claim:

1. A medical valve having an open mode that permits fluid flow and a closed mode that prevents fluid flow, the valve being capable of transitioning between the open mode and the closed mode, the medical valve comprising:

a housing having an inlet and an outlet;

a fluid channel extending between the inlet and the outlet, the fluid channel having a variable volume region and a total channel volume; and a translating member secured to the housing and at least partly bounding the variable volume region, the translating member being spaced from the inlet, the translating member having at least a portion that moves distally when the valve transitions from the closed mode to the open mode, the distal movement of the translating member enlarging the volume of the variable volume region and the total channel volume.

2. The medical valve as defined by claim 1 wherein the translating member is substantially coaxial with the majority of the fluid channel.

3. The medical valve as defined by claim 1 wherein the translating member includes a securing portion that normally maintains the at least a portion of the translating member in a position that minimizes the volume of the variable volume region.

4. The medical valve as defined by claim 3 wherein the securing portion stretches when the valve transitions from the closed mode to the open mode, and retracts when the valve transitions from the open mode to the closed mode.

5. The medical valve as defined by claim 1 wherein the fluid channel includes a translating fluid channel extending through the translating member, the translating fluid channel having substantially the same shape in both the open and closed modes.

6. The medical valve as defined by claim 1 wherein the translating member comprises a bellows.

7. The medical valve as defined by claim 1 wherein the translating member includes a compressible portion that compresses when the valve transitions from the closed mode to the open mode.

8. The medical valve as defined by claim 1 wherein the valve includes a swabbable seal.

9. The medical valve as defined by claim 1 wherein the valve is a luer activated valve.

* * * * *